United States Patent [19]
Brown et al.

[11] Patent Number: 5,578,828
[45] Date of Patent: Nov. 26, 1996

[54] FLAME SENSOR WINDOW COATING COMPENSATION

[75] Inventors: Dale M. Brown, Schenectady; Gerald J. Michon, Waterford, both of N.Y.

[73] Assignee: General Electric Company, Schenectady, N.Y.

[21] Appl. No.: 339,845

[22] Filed: Nov. 15, 1994

[51] Int. Cl.$^6$ ............................ G01J 1/42; G01J 5/10; F02C 9/28
[52] U.S. Cl. .................. 250/342; 250/339.15; 250/340; 250/353; 250/372; 356/315; 340/500; 340/513; 340/578; 340/600; 60/39.11
[58] Field of Search ..................... 250/342, 339.15, 250/340, 353, 372; 356/315; 340/500, 513, 578, 600; 60/39.11

[56] References Cited

U.S. PATENT DOCUMENTS

| | | | |
|---|---|---|---|
| 3,740,154 | 6/1973 | Green | 356/85 |
| 3,952,196 | 4/1976 | Larsen | 324/51 |
| 4,358,952 | 11/1982 | Maure et al. | 73/35 |
| 4,405,234 | 9/1983 | Juaire | 356/239 |
| 4,672,324 | 6/1987 | van Kampen | 328/6 |
| 5,093,576 | 3/1992 | Edmond et al. | 250/370.01 |
| 5,103,096 | 4/1992 | Wong | 250/339.12 |
| 5,257,496 | 11/1993 | Brown et al. | 60/39.06 |
| 5,303,684 | 4/1994 | Brown et al. | 123/435 |

*Primary Examiner*—Constantine Hannaher
*Assistant Examiner*—Virgil O. Tyler
*Attorney, Agent, or Firm*—Marvin Snyder

[57] ABSTRACT

Intensity of optical emission from a combustion flame within a gas turbine combustor is monitored through an optical window in the combustor wall by a primary detector. Because the window is susceptible to becoming coated with deposits during combustor operation, compensation for presence of a coating is achieved by directing illumination from an optical signal source, such as a silicon carbide light-emitting diode, into the window for internal reflection at an optical interface defined by the combustion side surface. A compensation detector, such as a silicon carbide photodiode, detects intensity of the internally reflected illumination as an indicator of the window coating thickness. The compensation detector is located at a non-combustion side of the window, along with a reference detector that responds to intensity of optical signal source illumination reflected from the non-combustion side surface of the window. An AC coupled differential synchronous detector circuit processes the compensation detector and reference detector output signals to compensate the primary detector output signals for the coating.

19 Claims, 3 Drawing Sheets

FLAME SENSOR WINDOW COATING COMPENSATION

This application is related to E. Y. Shu et al. patent application Ser. No. 08/339,843 filed concurrently herewith and assigned to the instant assignee.

BACKGROUND OF THE INVENTION

This invention relates generally to methods and apparatus for monitoring optical emissions from a flame within the combustor stage of a gas turbine engine through a window and, more particularly, to a method and apparatus for compensating for degradation in the transmission of optical emissions due to coatings on the window.

Gas turbines are extensively used as power plants for a wide diversity of applications including, as examples, electric power generators in utility power plants, land based engines for gas fired electrical generator or pipeline compressors, and shipboard or airborne engines for, respectively, marine or aeronautical propulsion.

Gas turbines burn hydrocarbon fuel which may include natural gas or kerosene, which is used as an aviation (jet) fuel. As a result of the combustion process, such turbines emit an exhaust stream containing a number of combustion products, including various forms of nitrogen oxide, collectively referred to as "$NO_x$", which is considered a pollutant.

It is widely known that, for a gas turbine, $NO_x$ emissions increase significantly as the combustion temperature rises. It is also known that operating a turbine in a so-called "lean burn" condition, which involves use of a lean mixture of fuel and combustion air (i.e., a relatively low fuel-to-air ratio), reduces the combustion temperature to a level that significantly reduces $NO_x$ emissions.

Brown et al. U.S. Pat. No. 5,257,496, issued Nov. 2, 1993, entitled "Combustion Control for Producing Low $NO_x$ Emissions Through Use of Flame Spectroscopy" and related Brown patent application Ser. No. 08/226,528, filed Apr. 12, 1994, also entitled "Combustion Control for Producing Low $NO_x$ Emissions Through Use of Flame Spectroscopy", both of which are assigned to the instant assignee, disclose closed loop feedback control systems which achieve a lean burn by employing a silicon carbide (SiC) photodiode to sense combustion temperature through measurement of the intensity of ultraviolet radiation from a combustion flame and continuously adjusting the fuel/air ratio of the fuel mixture such that the ultraviolet radiation intensity remains below a predetermined level associated with a desired low level of $NO_x$ emissions. Photocurrent produced by the photodiode is proportional to the photon flux produced by the flame and impinging on the photodiode.

The SiC photodiode itself is not actually located within the gas turbine combustor. Rather, an optical window is provided in a wall of the combustor, thus separating a combustion side region from a non-combustion side region, and the SiC photodiode or other suitable detector "views" the combustion flame through this window.

The window surface on the combustion side has the potential for becoming coated, over time, with materials such as carbon as a result of the high temperature, high pressure combustion process, thereby effectively degrading the transmission of optical emission from the combustion flame through the window.

While such degradation is not of particular concern in a simple on/off flame detection application, a potential problem is presented when optical emissions from the combustion flame are sensed for more sophisticated control purposes, such as the sensing of flame intensity as disclosed in Brown et al U.S. Pat. No. 5,257,496 and Brown patent application Ser. No. 08/226,528, with control of the combustor fuel-to air ratio being based in part on the sensed emission intensity. As another example, Shu et al. application Ser. No. 08/339,843, filed concurrently herewith, entitled "Optical Sensing of Combustion Dynamics", discloses a system wherein AC components at acoustic frequencies in the photodiode detector output signal, which correspond to various combustion dynamic frequencies, are recognized for monitoring and controlling combustion dynamics.

SUMMARY OF THE INVENTION

Accordingly, an object of this invention is to compensate for degradation in transmission of optical emission passing from a combustion flame through a window and caused by deposits that coat the window surface on the combustion side.

Briefly, in accordance with the invention, a light beam is directed into an optical window in a gas turbine combustor through the non-combustion side surface of the window and reflected from an optical interface defined by the combustion side surface of the window. An optical signal source such as a 6H SiC LED (light-emitting diode) is located at the non-combustion side of the window for producing the light beam that is directed through the non-combustion side surface of the window into the window itself, for internal reflection at the combustion side surface of the window back through the non-combustion side surface of the window into the non-combustion side region where it is sensed by a suitably positioned compensation detector, such as a silicon photodiode or a 3C SiC photodiode. Presence of a coating directly on the combustion side surface of the window reduces the amount of internal reflection at the interface defined by this surface. The reduction in intensity of the reflected light beam can be sensed to produce a window coating compensation signal as an indicator of the coating thickness and, with suitable calibration, the compensation detector can be employed to compensate for the correspondingly reduced signal produced by the primary detector which is located at the non-combustion side of the window and is responsive to optical emission from the combustion flame within the combustor. Thus an output signal from the compensation detector can be applied to the same turbine control circuitry which is responsive to the output signal of the primary detector, and employed to compensate for variations in the output signal of the primary detector which are due to deposits that coat the combustion side surface of the window.

Preferably, illumination by the combustion flame itself, as well as variations in the output beam of the optical signal source, are compensated for by a "common mode" rejection arrangement. Thus a reference detector is positioned at the non-combustion side region for responding to the intensity of illumination from the optical signal source, and preferably for responding to illumination from the optical signal source which is reflected from the non-combustion side surface of the optical window. The outputs of the window coating compensation detector and the reference detector accordingly are connected to opposite inputs of a differential detector so as to produce a corrected window coating compensation signal which is thus optimally dependent only on the degree of window coating.

To enhance the operation of this "common mode" rejection arrangement, it is preferred that the compensation detector and the reference detector both be responsive only to illumination from the optical signal source and reflection from both surfaces of the window, and not to the combustion flame itself.

Thus, the compensation detector and the reference detector are both positioned so as to avoid being directly illuminated by the combustion flame. (Exposure to indirect illumination by the combustion flame to some extent is unavoidable, and placing these two detectors next to each other at least gives such illumination a "common mode" characteristic.) Further, the optical signal source is driven from an AC power source, and the outputs of the compensation detector and of the reference detector are connected to a synchronous detector circuit which operates at the frequency of the AC power source, thus providing enhanced discrimination against extraneous light sources such as are produced by the flame.

As another consideration, as briefly described above, and as described in detail in the above-referenced Shu et al. application Ser. No. 08/339,843, there are various combustion dynamic frequencies which result in AC signals at detector outputs. In accordance with the invention, the frequency of the AC power source and of the synchronous detector is selected so as to differ from any such combustion dynamic frequencies.

BRIEF DESCRIPTION OF THE DRAWINGS

The features of the invention believed to be novel are set forth in the appended claims. The invention, however, together with further objects and advantages thereof, may best be understood by reference to the following description taken in conjunction with the accompanying drawing(s) in which:

DETAILED DESCRIPTION

Figure 1:
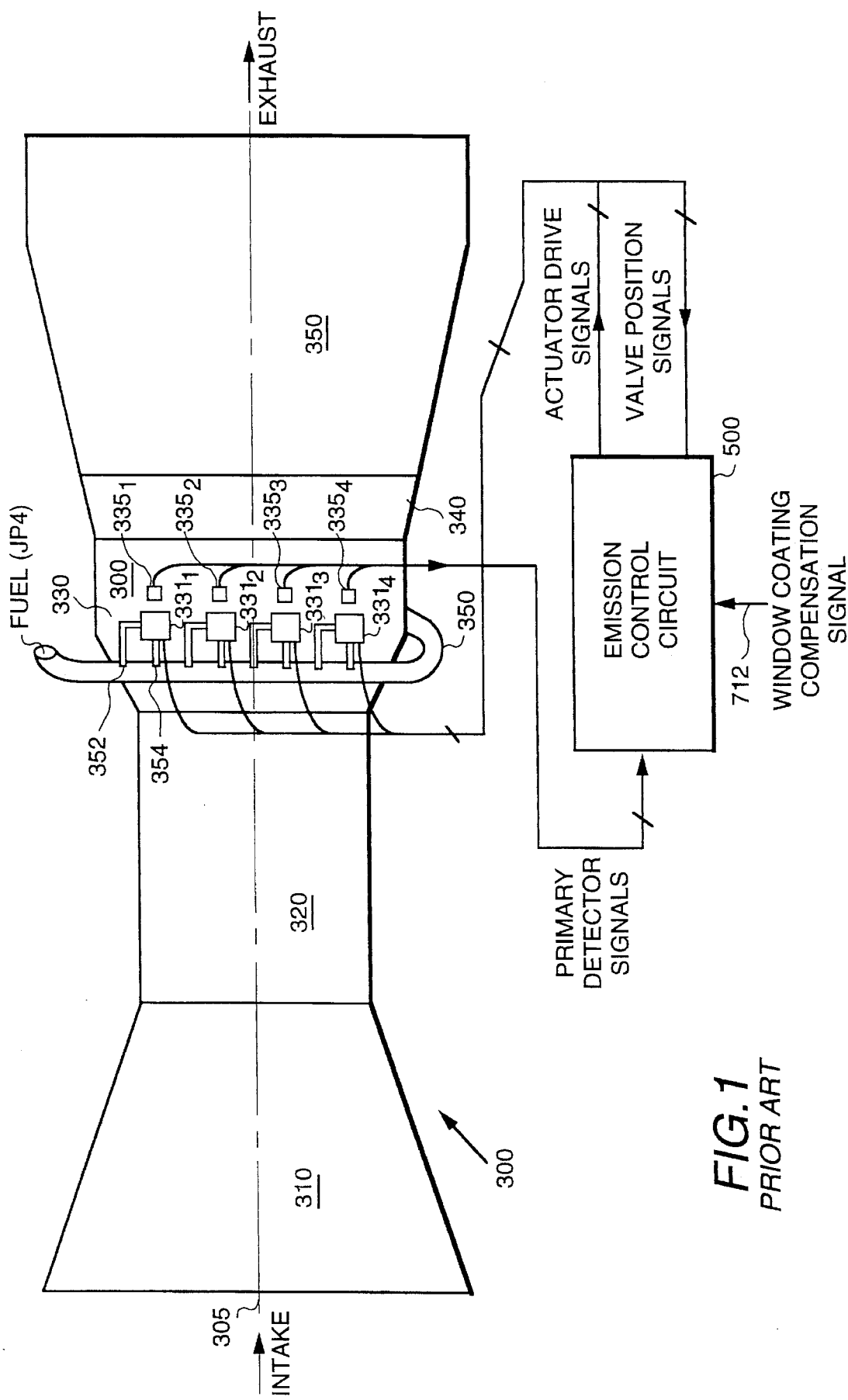
FIG. 1 is a simplified outline drawing of a jet engine incorporating the invention.

FIG. 1 is a simplified outline drawing of an aircraft jet engine 300 such as that shown and described in the above-identified Brown et al. U.S. Pat. No. 5,257,496 and Brown Patent application Ser. No. 08/226,528. Jet engine 300 incorporates flame intensity feedback control in accordance with the inventions of U.S. Pat. No. 5,257,496 and application Ser. No. 08/226,528, as well as compensation for window coatings in accordance with the present invention.

Jet engine 300 contains five successive coaxially aligned conventional stages: low pressure compressor stage 310, high pressure compressor stage 320, combustor 330, high pressure turbine stage 340 and low pressure turbine stage 350. Collectively, low and high pressure compressor stages 310 and 320 compress incoming intake air to a desired high pressure for use as combustion air. Combustor 330 injects jet fuel, e.g. JP-4, into the combustion air, using a series of fuel injectors, and establishes controlled internal combustion of the resulting fuel/air mixture. Hot expanding exhaust gases generated by the combustion are successively routed to high and low pressure turbine stages 340 and 350, respectively, which collectively extract power from the exhaust gases to suitably drive compressor stages 310 and 320 through common shafting (not shown). The gases expelled by low pressure turbine stage 350 exit the engine as exhaust. Since stages 310, 320, 340 and 350 are conventional, they are not discussed in greater detail herein.

Combustor stage 330 contains a series of fuel injector assemblies 331, formed of individual injector assemblies $331_1$, $331_2$, $331_3$, $331_4$, ... (of which only four are shown) situated at regular spacings completely around the periphery of an outer wall of the combustor stage and concentric with longitudinal axis 305 of the engine. Each of these assemblies, such as assembly $331_1$ which is discussed in greater detail below with reference to FIG. 2, includes a fuel injector which appropriately directs jet fuel into a combustion area, and a corresponding vernier valve to dynamically vary the fuel/air mixture for that particular fuel injector. The term "vernier valve" as used herein includes poppet valves which are positioned to be either opened or closed, for the purpose of finely adjusting the fuel supplied to the combustor flame.

Fuel manifold 350 is supplied with jet fuel from an appropriate fuel pump (not shown), and routes jet fuel in parallel to each of the injector assemblies. The fuel injectors and the corresponding vernier valves situated within the associated injector assembly are connected in parallel, through two separate fuel lines, to manifold 350, such as by fuel lines 352 and 354 for injector assembly $331_1$. If vernier valves are not employed, the amount of fuel supplied to each of the injectors is regulated by the diameter and length of the path traversed by the fuel through the manifold and associated fuel line, such as fuel line 354, and the flow rate at which fuel is pumped through the manifold to the engine. Ideally, since all the fuel lines that directly connect the fuel injectors to the manifold are approximately equal in size (both diametrically and lengthwise), all of the injectors should receive equal amounts of fuel directly from manifold 350. During engine manufacture and testing, the overall fuel/air mixture for the engine is set such that with, illustratively, all the vernier valves approximately half open, the engine operates in a desired lean-burn condition. This results in sufficiently high flame temperatures to prevent a flame-out condition but with substantially reduced levels of both CO and $NO_x$ emitted in the engine exhaust. Subsequently, each of the vernier valves is dynamically controlled to maintain the fuel/air mixture for its corresponding injector at a point such that the engine operates in the desired lean-burn condition.

In general, a primary radiation detector is secured to the outer wall of the combustion stage near each respective injector assembly and, through a suitable high temperature optical window, monitors that portion of the flame. Thus a detector assembly 335, formed of individual primary ultraviolet radiation detectors $335_1$, $335_2$, $335_3$, $335_4$, ... (only these four individual ultraviolet radiation detectors $335_1$, $335_2$, $335_3$ and $335_4$ are specifically shown) is mounted around the periphery of the outer surface of the combustion stage and concentric with longitudinal axis 305. Each individual primary ultraviolet radiation detector $335_1$, $335_2$, $335_3$, $335_4$, is mounted in the vicinity of a respective fuel injector assembly, though the exact spacing therebetween is not critical and, to some extent, is dictated by a designed flame geometry within the combustion stage.

In accordance with the inventions of U.S. Pat. No. 5,257,496 and application Ser. No. 08/226,528, the outputs of the individual primary ultraviolet radiation detectors $335_1$, $335_2$, $335_3$ and $335_4$ are routed to an emission control circuit 500. Briefly, circuit 500 generates suitable drive signals through use of both the output signals produced by the primary radiation detectors and valve position feedback signals produced by the fuel injector assemblies. Each drive signal is applied to a respective actuator (not shown) located within a corresponding fuel injector assembly. The respective actuator appropriately changes the position of an internal valve element within the vernier valve located in this assembly to increase or decrease the amount of fuel flowing to the corresponding injector and hence into the combustion chamber itself, thereby changing the fuel/air mixture associated with that injector. Each of the position feedback signals specifies the position of the valve element within the corresponding vernier valve. The position of each such element is thus dynamically adjusted to appropriately vary the fuel/air mixture for all the fuel injectors such that jet engine 300 continuously operates at a desired "lean-burn" condition.

In accordance with an aspect of the present invention, in addition to the detector signals, another input signal to emission control circuit 500 is a window coating compensation signal developed as described hereinbelow with reference to FIGS. 2 and 3. Briefly, emission control circuit 500, after suitable calibration, is responsive to the window coating compensation signal to compensate for primary radiation detector output signal variations which are due to deposits that form a coating on the combustion side surface of the optical window associated with each of primary radiation detectors $335_1$, $335_2$, $335_3$ and $335_4$.

Figure 2:
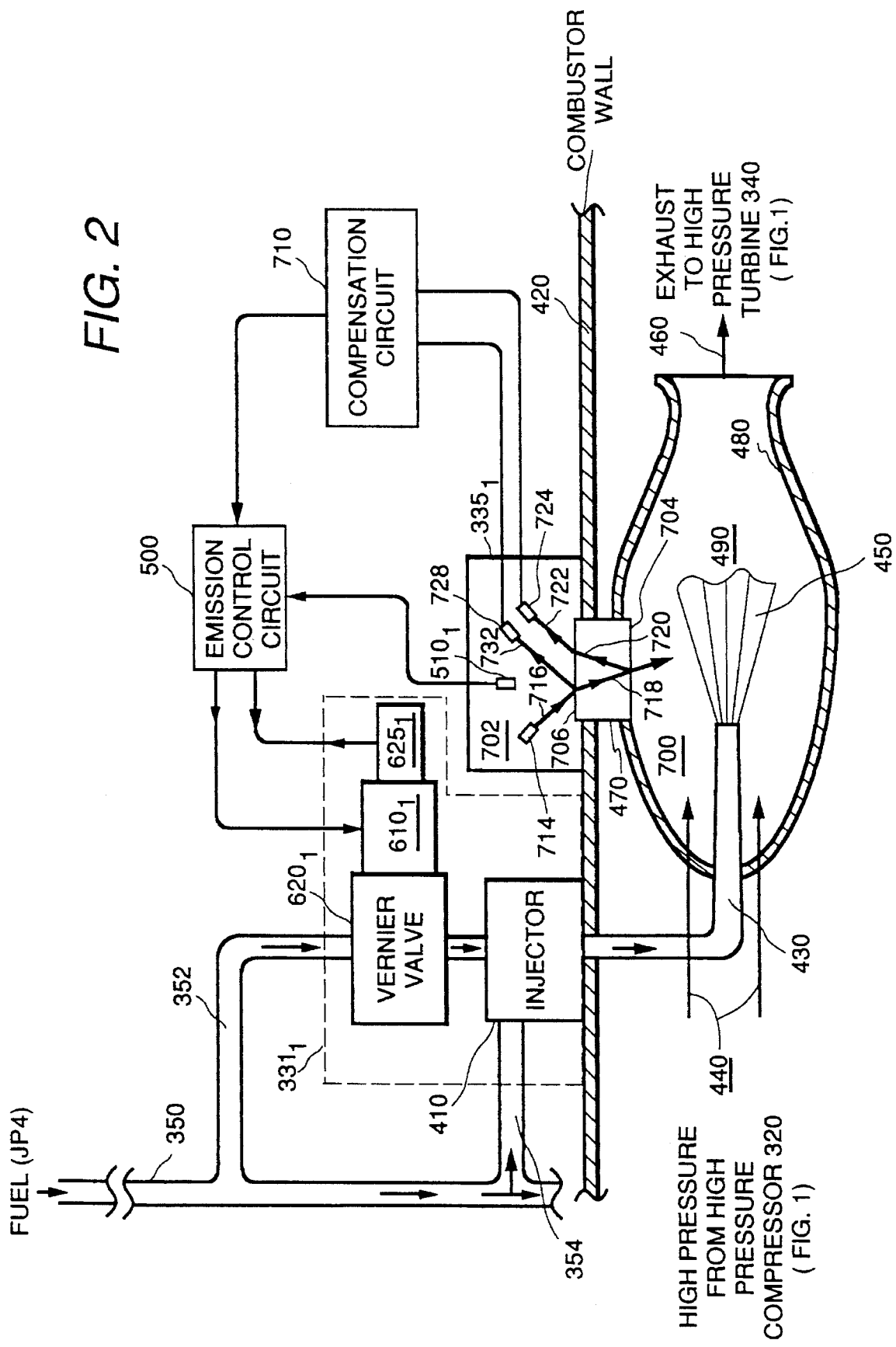
FIG. 2 is a simplified, partial sectional diagram of a portion of the combustor stage in the jet engine shown in FIG. 1.

FIG. 2 depicts a simplified, partly sectional diagram of a portion of combustor stage 330 in jet engine 300 shown in FIG. 1. As shown in FIG. 2, fuel injector assembly $331_1$ contains a vernier valve $620_1$, an actuator $610_1$, a position transducer $625_1$ and a fuel injector 410. Actuator $610_1$ has a common shaft (not shown) which is coupled both to an internal valve element within vernier valve $620_1$ and to position transducer $625_1$. The position of this shaft, monitored through the position transducer, sets the opening of the vernier valve.

Fuel injector 410 located within injector assembly $331_1$ is connected in parallel through two separate connections to fuel manifold 350: directly through fuel line 354, and via vernier valve $620_1$, through fuel line 352. Fuel flow occurs in the direction shown by the arrows within the fuel lines. Thus, based upon its setting, valve $620_1$ routes an additional amount of fuel to the injector beyond that flowing through fuel line 354. Injector 410 is joined with an injection nozzle assembly 430 which extends through combustor outer wall 420 and a flame shield 480 into combustion region 490. This nozzle assembly is oriented to spray fuel into a high pressure air stream 440 flowing through the combustion region. The sprayed fuel is ignited (through a conventional ignition device, not shown), resulting in a flame 450 within the combustion region, for which only a portion of the base of the flame is shown. The resulting combustion produces a hot exhaust gas stream 460 which is routed to high pressure turbine stage 340 (FIG. 1).

In order to monitor optical emissions produced by combustion flame 450, an optical window 470 associated with detector $335_1$ is appropriately mounted within combustor wall 420 and extends through flame shield 480. This window comprises any of a variety of appropriate well-known high temperature materials having suitable optical transmission characteristics, such as quartz or sapphire.

Optical window 470 thus separates a combustion side region 700 from a non-combustion side region 702, and represents a high pressure seal between high pressure (e.g. 250 psi) in the combustion region 700, and atmospheric pressure (e.g. 15 psi) in the non-combustion side region 702.

Optical window 470 has a combustion side surface 704 facing combustion side region 700. Surface 704 thus constitutes a combustion side interface with combustion side region 700. Interface 704 is, accordingly, an optical interface separating optical window 470, which has an optical index of refraction greater than 1, from combustion side region 700, which has a relatively lower optical index of refraction of approximately 1.0.

Similarly, optical window 470 has a non-combustion side surface 706 facing non-combustion side region 702, and likewise defines a non-combustion side interface 706 comprising an optical interface between the relatively higher index of refraction of window 470 and a region having an optical index of refraction nominally 1.0.

For detecting the intensity of optical emission from combustion flame 450, a primary optical radiation detector $510_1$, such as an SiC photodiode ultraviolet radiation detector, is located within non-combustion side region 702, conveniently contained within detector assembly $335_1$. Primary detector $510_1$ operates as described in the above-identified Brown et al. U.S. Pat. No. 5,257,496 and Brown patent application Ser. No. 08/226,528 to effect fuel-to-air ratio control for the purpose of maintaining "lean burn" conditions. Thus an output signal from primary detector $510_1$ is supplied to emission control circuit 500.

A suitable SiC photodiode, which is particularly useful for jet engine flame detection, is described in D. Brown et al. U.S. patent application "Silicon Carbide Photodiode with Improved Short Wavelength Response and Very Low Leakage Current," Ser. No. 07/878,937, filed May 5, 1992, abandoned in favor of continuation application Ser. No. 08/198,679, filed Feb. 18, 1994, now U.S. Pat. No. 5,394,005, issued Feb. 28, 1995 and assigned to the instant assignee. A silicon carbide photodiode is also disclosed in J. A. Edmond et al. U.S. Pat. No. 5,093,576, entitled "High Sensitivity Ultraviolet Radiation Detector."

SiC photodiodes are ideal sensors for working in a high temperature environment. SiC has a wide band gap and corresponding optical absorption and photo responsivity for wavelengths between approximately 200 nm and 400 nm, and accordingly does not respond to optical emissions in the visible and infrared range from black body radiation of the hot metal background within the gas turbine, as well as from hot particles which are part of the combustion flame. In comparison to silicon photodiodes, SiC photodiodes are stable at high temperatures, and require no special cooling. Further, SiC photodiodes take the form of rugged and compact solid state devices, which are easy to install and to maintain.

Being exposed to the combustion process, combustion side surface 704 of window 470 is susceptible to becoming coated with deposits during operation of combustor 330, effectively degrading transmission of optical energy emitted from combustion flame 450 through window 470 to detector $510_1$. While such degradation may not be a problem for gross control purposes, such as on/off flame detection, it has the potential for adversely affecting performance of emission control circuit 500.

In accordance with the invention, a compensation signal responsive to the degradation in transmission of optical energy from combustion flame 450 through window 470 is developed by a compensation circuit 710 and supplied as another input signal to emission control circuit 500. After appropriate calibration procedures, emission control circuit 500 compensates signals from primary radiation detector $510_1$ for coatings deposited on window 470 combustion side surface 704 during combustor operation. Exemplary signal compensation techniques include employment of computer corrective codes or automatic gain control of the signal from primary detector $510_1$. Although shown separately in FIG. 2, it will be appreciated that compensation circuit 710 may be included as part of emission control circuit 500.

An optical signal source 714, located within non-combustion side region 702, directs illumination 716 through non-combustion side interface 706 into window 470 as a refracted ray 718 which is then partially internally reflected at combustion side interface 704 as ray 720. Ray 720, after further refraction at non-combustion side interface 706, emerges from window 470 into non-combustion side region 702 as ray 722.

A compensation detector 724 positioned within non-combustion side region 702 responds to intensity of the refracted and reflected illumination represented by ray 722 to produce a window coating compensation signal as an indicator of coating thickness on combustion side interface 704 of window 470 which degrades transmission of optical emission from combustion flame 450 through the window. The output of compensation detector 724 is coupled to an input of compensation circuit 710.

The coating deposited directly on combustion side surface 704 and comprising an optical interface affects the amount of internal reflection of ray 718 within window 470. Thus the image of optical signal source 714 as viewed by compensation detector 724 decreases in intensity as thicker coatings are formed directly on combustion side surface 704 of the window.

As secondary compensation, in particular to implement a "common mode" rejection approach to signals resulting from indirect flame illumination of detector 724, and also to correct for variations in intensity of optical signal source 714, a reference detector 728 situated within non-combustion side region 702 is coupled to compensation circuit 710 and positioned to respond to intensity of illumination from optical signal source 714, which is reflected from non-combustion side interface 706 as ray 732, by providing a reference signal. Compensation circuit 710, by thus taking into account signals from both compensation detector 724 and reference detector 728, produces a corrected window coating compensation signal, which signal represents only minimal response to flame 450 illumination and is corrected for variations in intensity of illumination from optical signal source 714.

Since non-combustion region 702 is not exposed to combustibles and, furthermore, is sealed from the exterior environment, surface 706 remains clean, and the signal detected by reference detector 728 can be used as a reference.

Practical considerations involved in practicing the invention include appropriate selection of devices for signal source 714 and detectors 724 and 728. An LED may be employed as optical signal source 714. Although a silicon carbide (SIC) LED is presently preferred in view of the high temperature capability and reliability characteristics of SiC devices, a variety of other LED types may be employed, such as gallium arsenide or gallium phosphide. Appropriate cooling may be required when other than SiC devices are employed.

Silicon carbide is a compound semiconductor that exists in a relatively large number of different crystalline forms, of which the 6H form (with "H" representing hexagonal crystalline packing) is the most readily available. 6H SiC LEDs emit blue 500 nm light. Another form of SiC is "3C," which refers to a cubic crystal structure.

It will be appreciated that the optical wavelength response of detectors 724 and 728 must be consistent with the wavelength of optical emission from signal source 714. In the case of blue 500 nm illumination from a 6H SiC LED as illumination source 714, silicon photodiodes may be employed as detectors 724 and 728. (6H SiC photodiodes are not well suited for detection of blue 500 nm radiation produced by 6H SiC LEDs because SiC is not a direct transition material, and accordingly electron hole pairs created by forward biasing a SiC LED do not combine by direct transitions across the band gap but, rather, recombine via impurity level transitions. Thus the wavelength of light emitted by an SiC LED is longer than that which is produced by across-the-band-gap direct transitions.)

In the future, as suitable devices are developed, 3C SiC photodiodes could be used to advantage since the band gap is smaller than for 6H SiC, and the primary absorption edge is therefore moved to longer wavelengths. Thus a 3C SiC photodiode is compatible with illumination from a 6H SiC LED.

Other practical considerations involved in practice of the invention relate to prevention or minimization of interference in the optical compensation system comprising LED 714 and photodiodes 724 and 728, caused by optical emissions from flame 450 itself. An initial measure, relating to physical arrangement, is to position LED detectors 724 and 728 so as to avoid direct illumination by combustion flame 450; however, the physical arrangement must be such that at least partial internal reflection of ray 718 can occur at interface 704, and refractive transmission of ray 720 can occur through optical interface 706.

A closely related consideration is the positioning of reference diode 728 immediately adjacent compensation detector diode 724 such that detectors 728 and 724 respond to essentially parallel representative rays 732 and 722 coming from the direction of window 470, thus enhancing the capability of LED 728 to correct for variations in illumination intensity from optical signal source 714 when a differential detector circuit is employed in a common mode rejection arrangement.

As another practical consideration, and as described in detail in the above-referenced Shu et al. application Ser. No. 08/339,843, flame 450 exhibits vibration oscillations which produce AC components in detector $510_1$ output signals, as well as, potentially, in detector 724 and 728 output signals, to the extent that detectors 724 and 728 respond to illumination from flame 450. Even though not directly illuminated by flame 450, detectors 724 and 728 may be exposed to indirect flame 450 illumination. In accordance with the invention, LED 714 is driven from an AC power source which has a frequency different than that of expected combustion dynamic frequencies, and a synchronous detector circuit is employed.

Figure 3:
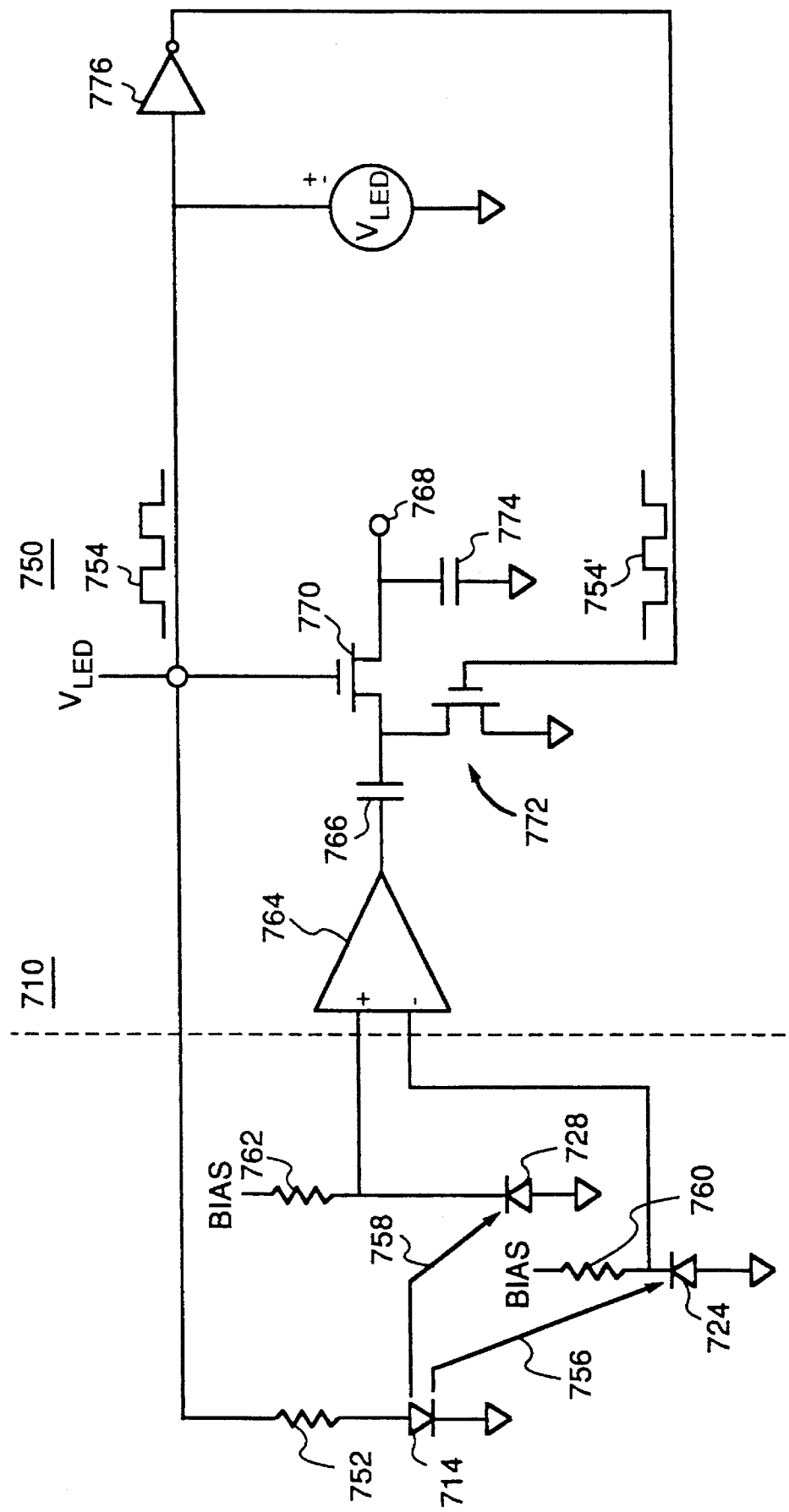
FIG. 3 is an electrical schematic diagram of an AC differential detector circuit.

More particularly, and with reference to FIG. 3, an AC differential detector circuit 750 is provided as part of compensation circuit 710 of FIG. 2. Thus LED 714 is driven through a current limiting resistor 752 via an AC drive signal $V_{LED}$ represented by waveform 754. The optical path represented by FIG. 2 rays 716, 718, 720 and 722 is represented by arrow 756, and the FIG. 2 optical path represented by rays 716 and 732 is represented in FIG. 3 by arrow 758.

Detectors 724 and 728 are appropriately biased through resistors 760 and 762, and are coupled to inputs of a differential amplifier 764 such that the output signal of reference detector 728 is subtracted from that of compensation detector 724. Amplifier 764 is AC coupled at its output as represented by capacitor 766.

Illustrating a synchronous detector arrangement, in series between capacitor 766 and a compensation signal output terminal 768 is a switching FET (field effect transistor) 770 driven with the same waveform 754 that excites LED 714, and shunting the output of capacitor 766 to ground is another switching FET 772 having its gate circuit connected to be driven by an inverse signal waveform 754' from an inverter 776. Thus the output signal of amplifier 764 is alternately switched on and off at the frequency of waveform 754. This AC coupled synchronous detector arrangement also eliminates the dark current DC signal of LEDs 724 and 728. A smoothing capacitor 774 is provided at output 768.

While only certain preferred features of the invention have been illustrated and described herein, many other modifications and changes will occur to those skilled in the art. It is, therefore, to be understood that the appended claims are intended to cover all such modifications and changes as fall within the true spirit and scope of the invention.

What is claimed is:

1. Apparatus for monitoring optical emission from a combustion flame within a gas turbine combustor through an optical window in a wall of the combustor separating combustion and non-combustion side regions, said window having a combustion side surface facing the combustion side region and defining a combustion side interface with the combustion side region, and said window having a non-combustion side surface facing the non-combustion side region and defining a non-combustion side interface with the non-combustion side region, said combustion side surface being susceptible to becoming coated with deposits during operation of the combustor thus effectively degrading transmission of optical emission from the combustion flame through said window, said apparatus comprising:

a primary detector located within the non-combustion side region for detecting intensity of optical emission from the combustion flame transmitted through both the combustion and non-combustion side surfaces of said window;

an optical signal source located within the non-combustion side region for directing illumination through the non-combustion side interface into said window; and a compensation detector positioned within the non-combustion side region for responding to intensity of any signal source illumination internally reflected at the combustion side interface and transmitted back through the non-combustion side interface to produce a window coating compensation signal as an indicator of coating thickness on said combustion side surface.

2. The apparatus of claim 1, further comprising turbine control circuitry responsive to an output signal from said primary detector, and responsive to the window coating compensation signal from the compensation detector to compensate for any reduction in the output signal from said primary detector due to presence of a coating on said combustion side surface.

3. The apparatus of claim 1, further comprising a reference detector positioned within the non-combustion side region for responding to intensity of illumination from said optical signal source to produce a reference signal.

4. The apparatus of claim 3, wherein said reference detector is positioned to produce said reference signal by responding to intensity of illumination from said optical signal source as reflected from said non-combustion side interface.

5. The apparatus of claim 3, further comprising a differential detector responsive to the window coating compensation signal from said compensation detector and responsive to the reference signal from said reference detector to produce a corrected window coating compensation signal that is corrected for illumination of said compensation detector by the flame and for variations in intensity of illumination from said optical signal source.

6. The apparatus of claim 5, wherein said reference detector is positioned to produce said reference signal by responding to intensity of illumination from said optical signal source as reflected from said non-combustion side interface.

7. The apparatus of claim 1, wherein said compensation detector is positioned to avoid direct illumination thereof by the combustion flame.

8. The apparatus of claim 3, wherein said compensation detector and said reference detector are each positioned so as to avoid direct illumination thereof by the combustion flame.

9. The apparatus of claim 1, wherein said combustion flame exhibits a combustion dynamic frequency and said optical signal source is driven from an AC power source having a frequency which differs from said combustion dynamic frequency.

10. The apparatus of claim 9, further comprising a synchronous detector coupled to receive signals from said compensation detector, said synchronous detector being coupled to operate at the frequency of the AC power source.

11. The apparatus of claim 1 wherein said optical signal source is driven from an AC power source, said apparatus further comprising a synchronous detector coupled to receive signals from said compensation detector, said synchronous detector being coupled to operate at the frequency of the AC power source.

12. The apparatus of claim 1, wherein said optical signal source comprises a silicon carbide light-emitting diode.

13. The apparatus of claim 12, wherein said compensation detector comprises a silicon photodiode.

14. The apparatus of claim 12, wherein said compensation detector comprises a silicon carbide photodiode.

15. A method of monitoring optical emission from a combustion flame within a gas turbine combustor through an optical window in a wall of said combustor, said window having a combustion side surface susceptible to becoming coated with a deposit during combustor operation, comprising the steps of:

detecting intensity of optical emission from the combustion flame transmitted through the combustion side surface of said window;

directing illumination from an optical signal source located outside said combustor through a non-combustion side surface of the window into the window for internal reflection at an optical interface defined by the combustion side surface;

detecting intensity of illumination from said optical signal source internally reflected in said window at the optical interface defined by the combustion side surface; and compensating the detected intensity of optical emission from the combustion flame for the detected intensity of illumination from said optical signal source internally reflected in said window.

16. The method of claim 15, comprising the additional steps of detecting intensity of illumination from said optical signal source reflected from the non-combustion side surface of said window, and compensating the detected intensity of optical emission from the combustion flame for the detected intensity of illumination reflected from the non-combustion side surface of the window.

17. The method of claim 15, comprising the additional steps of detecting intensity of illumination from said optical signal source, and compensating the detected intensity of optical emission from the combustion flame for variations in intensity of illumination from said optical signal source.

18. The method of claim 16, comprising the additional steps of driving the optical signal source from an AC power source, and employing a synchronous detector operating at the frequency of the AC power source to process signals representing the detected intensity of illumination from said optical signal source reflected from the non-combustion side surface of the window and the detected intensity of said illumination from said optical signal source that is internally reflected in said window.

19. The method of claim 17, comprising the additional steps of driving the optical signal source from an AC power source, and employing a synchronous detector operating at the frequency of the AC power source to process signals representing the detected intensity of illumination from said optical signal source and the detected intensity of said illumination from said optical signal source that is internally reflected in said window.

* * * * *